United States Patent [19]
Petersen

[11] Patent Number: 5,882,931
[45] Date of Patent: Mar. 16, 1999

[54] METHOD AND APPARATUS FOR PERFORMING URINALYSIS IN REAL TIME

[76] Inventor: Roger Petersen, Houston, Tex.

[21] Appl. No.: 892,249

[22] Filed: Jul. 14, 1997

[51] Int. Cl.[6] .............................. G01N 21/00; A61B 5/00
[52] U.S. Cl. .......................... 436/55; 422/55; 422/82.05; 422/108; 600/584
[58] Field of Search ..................... 600/584; 422/82.01, 422/82.02, 82.03, 82.04, 82.05, 82.06, 82.07, 82.08, 82.09, 82.12, 55, 108; 436/151, 164, 169, 55

[56] References Cited

U.S. PATENT DOCUMENTS

| | | | |
|---|---|---|---|
| 4,636,474 | 1/1987 | Ogura et al. | 600/584 |
| 4,961,431 | 10/1990 | Ikenga et al. | 600/584 |
| 5,001,048 | 3/1991 | Taylor et al. | 436/151 |
| 5,198,192 | 3/1993 | Saito et al. | 422/68.1 |
| 5,250,439 | 10/1993 | Musho et al. | 436/151 |

Primary Examiner—Jeffrey Snay
Attorney, Agent, or Firm—Gunn & Associates, P.C.

[57] ABSTRACT

A PCB supporting electronics is potted in a resilient sheet of material having an adhesive back face glued to a urinal below the flush water outlet. The front face is a target for a urine stream; it supports a urine sensor, say a temperature sensor. Added sensors measure urine characteristics as it flows over the face. Residue is flushed away. The PCB supports a data processing circuit. The output is sent to a remote indicator.

23 Claims, 3 Drawing Sheets

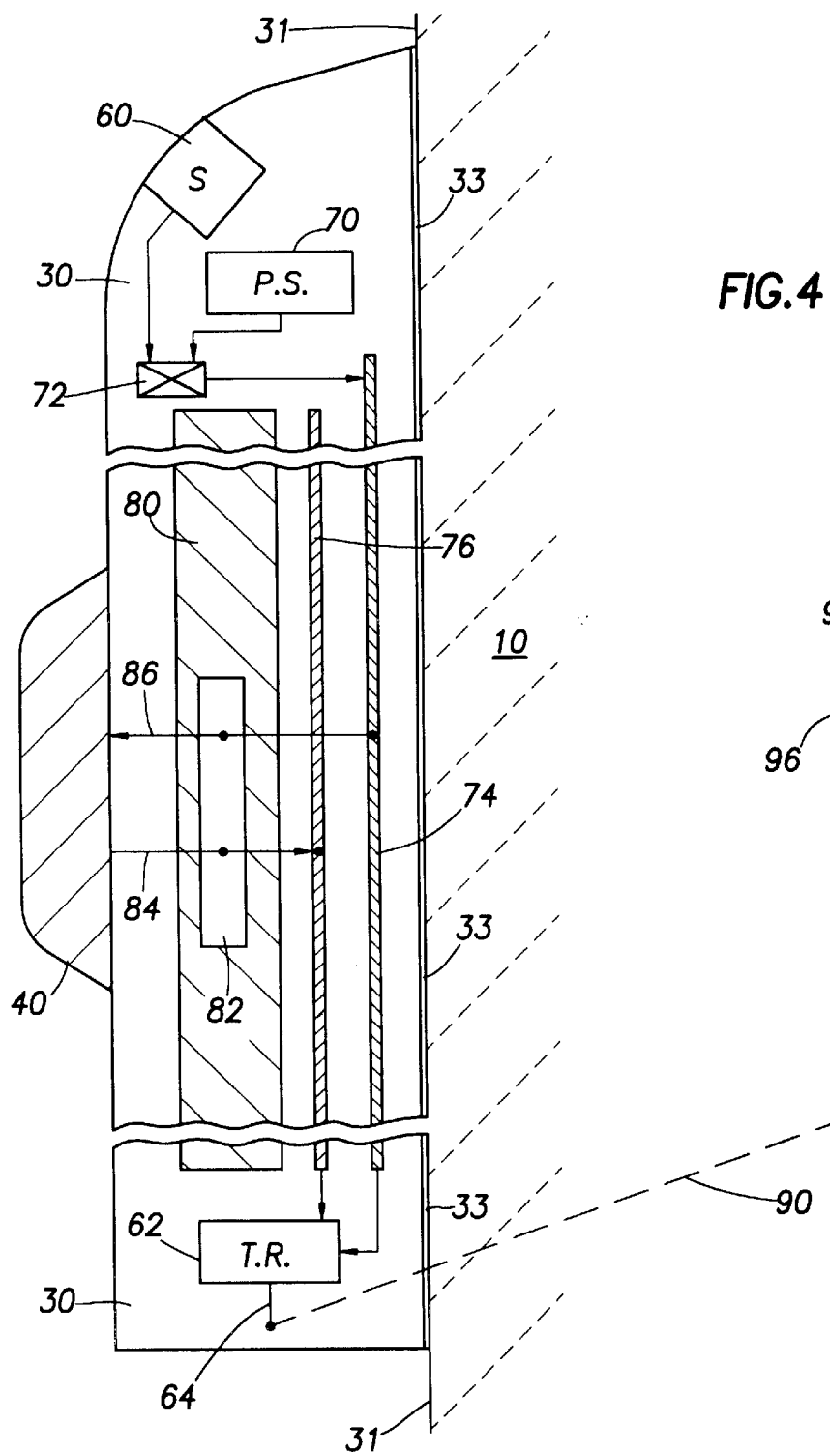
FIG.4
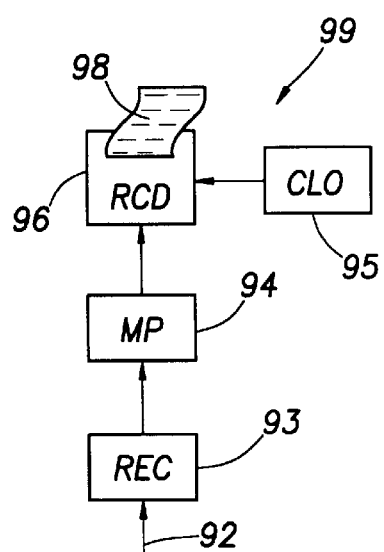

METHOD AND APPARATUS FOR PERFORMING URINALYSIS IN REAL TIME

BACKGROUND OF THE INVENTION

This disclosure is directed toward apparatus and methods for performing analytical test on samples of urine. More particularly, the invention is directed toward performing the tests using apparatus which is mounted within a urinal to receive urine samples, which makes measurements on the received samples, and which transmits results to a remote location for recording and further study.

Modern diagnostic medicine uses as a foundation in vivo testing and in analytical testing of material secreted by the body. Examples of in vivo testing include x-ray, ultrasound, magnetic resonance imaging (MRI), and injected radioactive scans such as coronary imaging using radioactive thallium injected into the blood stream. Examples of secreted material testing include the analysis of blood samples drawn from the patient, the analysis of urine samples given by the patient, and the like. With the possible exception of ultrasonic imaging, most in vivo tests are typically analyzed and interpreted subsequent to testing. The time lapse between testing typically ranges from a few hours to a few weeks. The time interval between the collection and the analysis and the interpretation of analytical results of secreted samples typically ranges from a few days to a few weeks.

Attention is now directed toward the analysis of urine, which is commonly referred to as "urinalysis". The analysis of a patient's urine samples provides a physician with a wealth of information concerning the health of a patient. The detection of abnormal levels of sugar and ketones can indicate a diabetic condition. The detection of blood in the urine can indicate urinary tract problems. A measure of conductivity can be used to indicate the level of the patient's electrolytes. Total dissolved solid (TDS) content can indicate certain kidney and bladder problems. There are numerous additional urinalysis tests which are well known in the art, and the interpretation of these tests are well known in the medical art.

In addition to diagnostic medical tests, urine is often analyzed to determine if the patient is taking either legal or illegal drugs. Urine tests which indicate the subject's use of marijuana is well known in the art. There are other urinalysis tests for the use of cocaine use and other illegal drugs.

As mentioned previously, the time lapse between the collection of a urine sample and the "off-site" analysis of the urine sample can be quite long. Additional time is typically required for a technician or physician to interpret the analytical results. This time delay can delay treatment of a patient in the event that the urinalysis indicates an abnormal condition or conditions. If the urinalysis is being used as an illegal drug screen, the delay in analysis and further delay in interpretation can be quite detrimental. If an illegal drug screen is performed by a company as a precursor to hiring, the employment process can be delayed for days or weeks by waiting for urinalysis results. If employees are routinely screened for illegal drugs, delay in urinalyses results could result in a drug abusing employee performing a critical job tests for weeks before drug screen results are obtained by the employer.

It is very desirable to perform diagnostic medical urinalysis on a routine basis. Such routine analyses can be used as periodic "scans" for symptoms of diabetes, kidney, bladder and other types of disease. This would provide an early warning of the onset of the disease thereby allowing diagnosis and treatment to be initiated as early as possible. Real time interpretation of such scans would also accelerate the diagnosis process thereby allowing the earliest possible treatment of a detected condition.

Urinalysis for illegal drugs on a routine basis is also highly desirable in that it would serve as a deterrent for illegal drug use. Furthermore, the interpretation of urinalysis results in real time would further serve as a deterrent, and rapidly identify "users" so that they can be removed as employees, receive treatment for the condition, or be dismissed from employment.

In view of the preceding background discussion, and object of the present invention is to provide apparatus and methods for routinely performing urinalysis by sampling urine at one or more urinals.

An additional object of the invention is to provide apparatus which can be attached to existing urinals to collect and analyze urine samples.

Another object of the invention is to provide an apparatus which can be used to sample and analyzes urine from a plurality of users of the urinal.

Yet another object of the invention is to provide a real time urinalysis system which is automatically activated by the use of the urinal and automatically purged for the next user and deactivated when the urinal is "flushed", enabling resetting.

Another object of the invention is to provide apparatus for automatically telemetering a plurality of urinalysis results from a plurality of equipped urinals to a central, remote location for recording and further analysis and reporting.

There are other objects of the invention which will become apparent in the following disclosure.

SUMMARY OF THE INVENTION

This disclosure sets forth a system for routine and automatic urinalysis. Urine samples are received by an apparatus which is affixed to the exposed, vertical wall of a standard urinal. This apparatus contains one or more analysis sensors which respond to the components of the urine to be measured. As an example, analysis sensors can be selected such that one sensor responds to sugar level, another sensor responds to ketones, another sensor responds to conductivity, another sensor responds to blood, and another sensor responds to TDS.

The analysis sensors are preferably activated and deactivated by a temperature sensor mounted on the urinal apparatus. Ambient temperature of the urinal is controlled such that it falls between normal human body temperature of 98.6 degrees Fahrenheit (°F.) and the temperature of the water used to flush the urinal (typically 60° F.). The temperature sensor cooperates with a switch such that the analysis sensors are activated when relatively warm (~98° F.) urine impinges upon the temperature sensor. The urine cascades over the analysis sensors thereby permitting the desired analyses to be made. When the urinal is flushed, the relatively cool water cascades over the preferred temperature sensor thereby deactivating the analysis sensors. The flush water also purges the analysis sensors and makes them ready to receive the next urine sample.

Electrical power for the sensors is preferably supplied to the temperature and the analysis sensor by a battery mounted within the urinal apparatus. Alternately, power from and external source, such as "house" power of a building housing the urinal, can be used to power the components within the urinal apparatus.

The urinal apparatus contains a printed circuit board which provides the necessary electronic controls and analysis means for the analysis sensors. As an example, if the measured sensor responds to conductivity of the urine, the sensor surface will preferably contain a positive, a negative and a current electrode. All electrodes contact the urine. The portion of the printed circuit board contains means for measuring current within the urine sample. That portion of the printed circuit board also contains a simple microprocessor for converting the measured current into urine conductivity and preferably into a unit indicative of the patient's electrolyte level. Other portions of the printed circuit board service other analysis sensors as will be described in subsequent sections of this disclosure.

The urinal apparatus also contains a transmitter which is used to transmit analysis results, measured by the analysis sensors and processed by one or more microprocessing means on the circuit board, to a remote facility. The remote facility preferably includes a receiver to receive the telemetered data, and a microprocessor to direct and index data from multiple users of multiple urinals. The remote facility also consists of means for recording the transmitted results, and means such as a clock for tracking when the results are received.

Power is preferably supplied to the temperature sensor, the analysis sensors, components of the PCB and the transmitter by means of a common power source cooperating with a power bus within the PCB card. Response data from the various sensors is preferably multiplexed and input to the urinal apparatus transmitter by means of a data bus within the PCB card.

Analysis sensors fall primarily into two categories which are defined as a contact type and a flow through type. For the contact type, urine is retained within a porous, highly permeable outer layer of the sensor for measuring, and subsequently is purged by the flush water. In the flow through type, urine cascades through conduits within the outer face of the sensor. Measurements are made in the flowing urine, which is subsequently purged by the flush water.

BRIEF DESCRIPTION OF THE DRAWINGS

So that the manner in which the above recited features, advantages and objects of the present invention are attained can be understood in detail, more particular description of the invention, briefly summarized above, may be had by reference to the embodiments thereof which are illustrated in the appended drawings.

It is to be noted, however, that the appended drawings illustrate only typical embodiments of the invention and are therefore not to be considered limiting of its scope, for the invention may admit to other equally effective embodiments.

FIG. 4 is a more detailed cross sectional view of the urinalysis apparatus, and a functional diagram of a remote station which receives data transmitted from one or more urine samples analyzed by one or more urinalysis apparatuses;

DETAILED DESCRIPTION OF THE PREFERRED EMBODIMENTS

Figure 1:
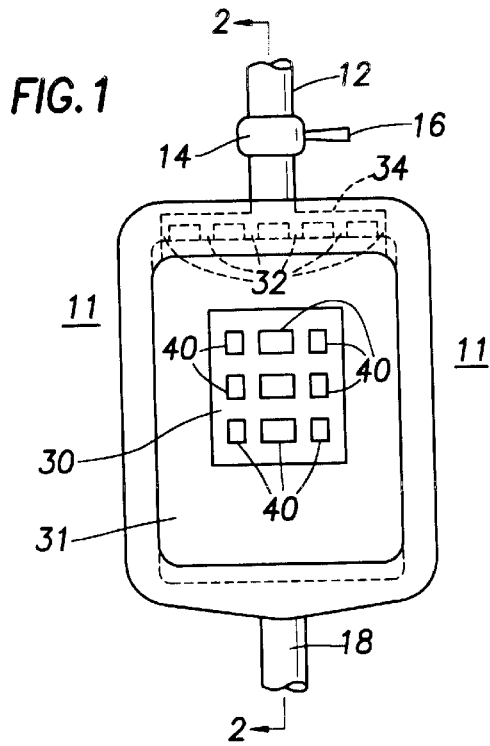
FIG. 1 is a frontal view of a urinal in which a urinalysis apparatus is mounted.

Attention is directed to FIG. 1 which shows a frontal view of existing, unmodified or "standard" urinal 10 mounted on a wall 11. Water enters the urinal through an input pipe 12 and passes through a flush valve 14 which is activated by a flush handle 16. When flushed, water enters a compartment 34 and exits through a plurality of flush holes 32 and subsequently cascades down an inner vertical wall 31 of the urinal 10. Flush water, and any urine contain therewithin, exits the urinal through a drain and drain pipe 18 which is connected to a standard sewage system (not shown).

Figure 2:
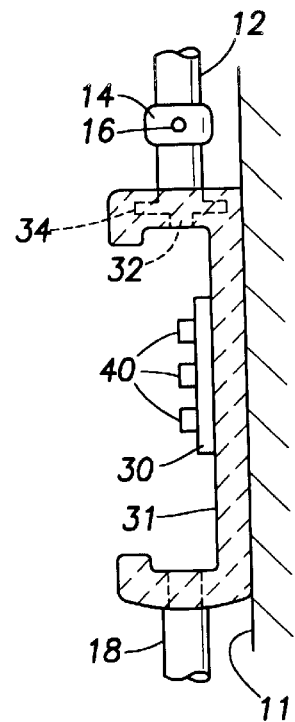
FIG. 2 is a cross sectional view of a urinal in which a urinalysis apparatus is mounted.

Still referring to FIG. 1, urine samples are received by a urinal apparatus 30 which is affixed to the vertical wall 31 of the standard urinal 10. A cross sectional view of the urinal 10 and attached urine apparatus 30 at A–A' is illustrated in FIG. 2. A suitable, water proof adhesive material 33 is used to affix the urinal apparatus 30 to the wall 31 so that the urinal apparatus can be remover for service or replacement without damage to the urinal wall. Referring to both FIGS. 1 and 2, the apparatus 30 contains one or more analysis sensors 40 which respond to the components of the urine to be measured. As an example, a first analysis sensors can respond to sugar, a second sensor can respond to ketones, a third sensor responds to conductivity, and fourth sensor can responds to blood, and so forth.

It should be understood that the urinal design shown in FIGS. 1 and 2 is typical, but the invention can be used equally effectively with urinals with varying designs.

Figure 3:
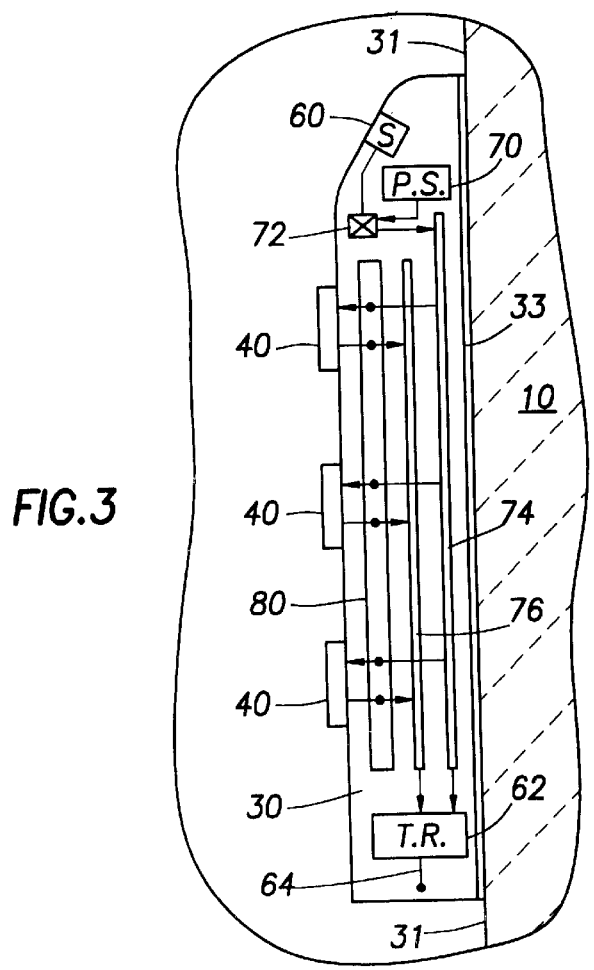
FIG. 3 is a cross sectional view of the urinalysis apparatus showing major components.

Attention is next directed to FIG. 3 which illustrates an enlarged cross sectional view of the urinal apparatus 30, attached sensors 40, and additional components to be defined. The analysis sensors 40 are activated and deactivated preferably by a temperature sensor 60 mounted preferably near the top of the urinal apparatus 40, and recessed within a curved upper edge of the urinal apparatus 40 to enhance a relatively uniform fluid flow down the face of the urinal apparatus 30. The urinal 10 is preferably mounted in a controlled climate facility, such as a typical restroom, where the ambient temperature of the urinal falls between normal human body temperature of 98.6° F. and the temperature of the water used to flush the urinal which is typically 60° to 65° F. The temperature sensor 60 closes a switch 72 to apply power to the analysis sensors 40 when urine, which is warmer (~98° F.) than the ambient temperature, impinges upon or flows across the temperature sensor. The urine also cascades over the analysis sensors 40 thereby permitting the desired analyses to be made. When the urinal is flushed by opening the valve 14 by means of the handle 16, flush water, which is cooler than ambient temperature, cascades over the temperature sensor 60. The temperature sensor responds to the cooler temperature by opening the switch 72 thereby deactivating the analysis sensors 40. The flush water also purges the analysis sensors 40, as will be discussed later, and makes them ready to receive the next urine sample.

In an alternate embodiment, the sensor 60 is an acoustic sensor of the type used in the prior art to automatically flush urinals. The acoustic type sensor emits acoustic waves. An approaching user of the urinal reflects a portion of the emitted waves, and these waves are sensed by the sensor 60 and used as a signal to activate the urinal apparatus 30. When the user departs the urinal, reflected waves are no longer senses by the sensor 60 thereby providing a second signal for deactivating the urinal apparatus 30. This embodiment is preferred if the urinal 10 can not be housed within a controlled climate system.

Electrical power is preferably supplied to the temperature and the analysis sensors by a power supply 70 mounted within the urinal apparatus 40. The power supply is preferably a battery. Alternately, power from and external source, such as "house" power of the building, can be used to power the components within the urinal apparatus.

The urinal apparatus 30 contains a printed circuit board (PCB) 80 as shown in FIGS. 3 and 4. The body 30 can readily be a resilient sheet of material, which is impervious to urine or chemical attack. It is a potting material securing the components integrated within the body and between the front and back faces. The PCB 80 provides the necessary electronic controls and analysis means for the analysis sensors 40. Portions 82 of the PCB, as shown in the more detailed view of FIG. 4, are dedicated to specific analysis sensors 40 as will be explained in subsequent sections of this disclosure. The urinal apparatus 30 also contains a transmitter 62 and antenna 64 which is used to transmit analysis results, measured by the analysis sensors 40 and processed by one or more microprocessing means 126, 126' (see FIGS. 5 and 6) on the circuit board 80, to a remote facility indicated as a whole in FIG. 4 by the numeral 99. The electromagnetic transmission between the transmitter 62 and the remote location 99 is denoted symbolically by the dashed line 90, The remote facility 99 having a receiver 93 and associated antenna 92 to receive data telemetered from the transmitter 62 within the urinal apparatus 30. A remote microprocessor 94 cooperates with the receiver 93 to direct and index data from multiple users of multiple urinal apparatuses 30. The remote facility 99 also includes a means 96 for recording the analysis results 98. The recorder 96 is preferably a data tabulation device, or alternately a strip chart recording device. If the amount of received data is large, a magnetic disk recorder is preferred as a recording means 96 with the recorded results 98 being a magnetic disk. A timer means 95, such as a clock, cooperates with the recorder 96 to aid in tracking when transmitted data are received.

Referring again to FIGS. 3 and 4, power is preferably supplied to the temperature sensor 60, the analysis sensors 40, components of the PCB 80, and the transmitter 62 by means of a common power source 70 cooperating with a power bus 74 within the PCB. Response data from the various sensors 40 are preferably multiplexed, as will be subsequently discussed, and input to the transmitter 62 by means of a data bus 76 within the PCB 80.

Analysis sensors 40 typically fall primarily into two categories which are the contact type and the flow through type. These two types or classes of sensors will be discussed separately in the following paragraphs. It should be understood, however, that other types of sensors can be used in conjunction with the urinal apparatus 30.

Figure 5:
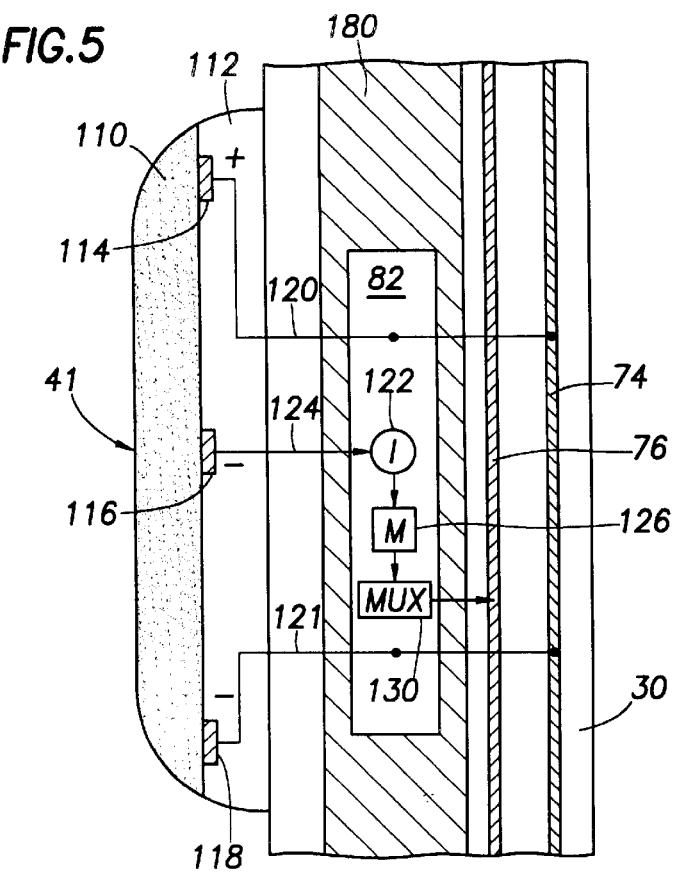
FIG. 5 is a cross sectional view of a contact type analysis sensor.

FIG. 5 is a cross sectional view of a contact type sensor, denoted as a whole by the numeral 41, mounted on the front face of the urinal device 30. In this type of sensor, urine is retained within a porous, highly permeable outer layer 110 of the sensor 41 for time sufficient to make the desired measurement. Subsequently, the urine is purged from the layer 110 by the flush water.

The contact sensor shown in FIG. 5 responds to conductivity of the urine. The sensor surface 110 is backed by a layer 112 which contains electrodes 114, 116 and 118 which contact the outer layer 112. These electrodes are, therefore, in electrical contact with any fluid within the porous and permeable outer layer 110. Contacts 114 and 118 are preferably positive and negative potential electrodes, respectively. Electrode 116 is a current electrode. All electrodes are connected to the portion 82 of the PCB 80 dedicated to the sensor 41. Specifically, electrodes 114 and 118 are connected by conductors 120 and 121, respectively, to the power bus 74 through the portion 82 of the PCB 80. Electrode 116 connects to a current meter 122 through a conductor 124. The measured current is input into a microprocessor 126 mounted on the portion 82 of PCB 80. Within the microprocessor 126, the measured current induced by the urine sample is converted into urine conductivity and preferably into a unit indicative of the patient's electrolyte level. The output of the microprocessor 126 is multiplexed in a multiplexer 128 and subsequently transferred by means of conductor 130 to the data bus 76 for transmission by transmitter 62 to the remote site 99.

Figure 6:
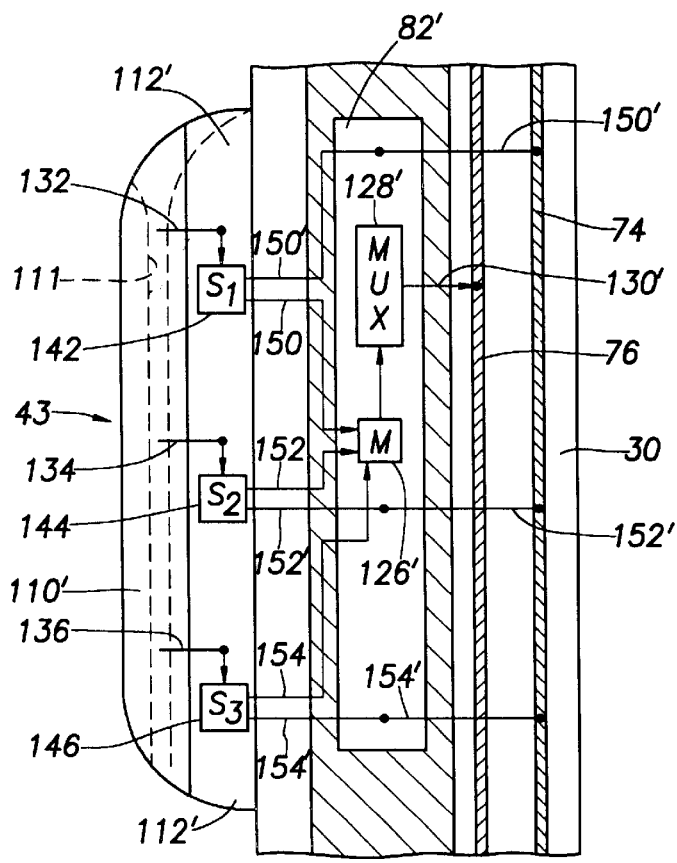
FIG. 6 is a cross sectional view of a flow through type analysis sensor.

A flow through type analysis sensor 43 is illustrated in cross section in FIG. 6. Urine cascades through one or more conduits 111 within an outer layer 110' of the sensor. Measurements are made in the flowing urine, which is subsequently purged by the flush water. One or more probes, each preferably designed to respond in a defined manner to a specific property of the urine, are inserted into the conduit 111 to contact the flowing urine. Three probes 132, 134 and 136 are illustrated as an example in FIG. 6. Responses of probes 132, 134 and 136 are preprocessed by the circuits 142, 144 and 146, respectively. Outputs from these circuits are then input by conductors 150, 152 and 154, respectively, to a microprocessor 126' mounted in portion 82' of the PCB 80. Outputs are converted within the microprocessor 126' into the measured parameters of interest (such as ketone level, sugar level, blood content, etc.), multiplexed in a multiplexer 128' within the portion 82', and subsequently transferred to the data bus 76 by means of conductor 130'. Power is preferably supplied to the sensor components 142, 144 and 146 from the power bus 74 through conductors 150', 152' and 154', respectively.

It is again emphasized that the analysis sensors illustrated in FIGS. 5 and 6 are examples, and other types of sensors can effectively be used. Circuits illustrated in FIGS. 5 and 6 are preferred, but alternate arrangements can be used in the invention. As an example, optical fibers rather than electrical conductors can be used to transfer analysis sensor responses to processing means mounted on the PCB 80. Other embodiments of the invention can be effectively used. As an additional example, a single microprocessor on the PCB 80 can be used to process responses from a plurality of analysis sensors 80. As a further example, the sensors 40 can be responsive to optical signals, such as the color of litmus reagents, rather than responsive to electrical signals. As an additional variation of the embodiment of the invention, analysis data can be recorded by a recording means (not shown) remote from the urinalysis apparatus 30, and these data can be retrieved and tabulated when the urinalysis apparatus is serviced. Data recording in a memory on the PCB avoids the transmitter 62 and the remote facility 99 would not be required.

While the foregoing disclosure is directed to the preferred embodiments of the invention, the scope thereof is determined by the claims which follow.

I claim:

1. Urinalysis apparatus comprising:
    (a) a planar member having
        (1) a back face for removable attachment to an existing urinal, wherein said existing urinal comprises
            a flush valve, and
            a vertical wall across which flows flush water when said flush valve is activated;
        (2) an exposed front face exposed to flush water for washing and also exposed to a urine stream;

(b) a sensor positioned on said exposed front face to contact the urine stream to measure a characteristic of urine;

(c) a circuit in said planar member connected to said sensor for forming a urine based signal; and (d) an output device responsive to the urine based signal;

wherein said sensor responds to temperature, said circuit has an active state and an off state, said urine based signal is formed while said circuit is in said active state, and said circuit is active dependent on a sensor measured temperature of contacting urine and off dependent on a sensor measured temperature of flush water.

2. The apparatus of claim 1 wherein said member is positioned below said flush water and above a drain in said urinal.

3. The apparatus of claim 2 wherein said front face includes a urine stream target.

4. The apparatus of claim 1 wherein said member is resilient and encloses said circuit, a power supply, and a transmitter sending the urine based signal to said output device.

5. The apparatus of claim 1 wherein circuit uses reduced power when not active and more power when active whereby reducing power consumption.

6. The apparatus of claim 1 wherein said sensor makes surface contact with urine.

7. The apparatus of claim 1 wherein said sensor absorbs urine prior to making a measurement and flush water removes absorbed urine.

8. The apparatus of claim 1 wherein said sensor funnels urine into an optical measurement.

9. The apparatus of claim 1 wherein said sensor makes surface contact and responds to a urine constituent.

10. The apparatus of claim 1 wherein said apparatus positions three sensors so that said three sensors form output signals indicative of three different urine characteristics, and said output signals are sent by said circuit to an output device responsive to said three characteristics and forms a urine measurement.

11. The apparatus of claim 1 wherein said circuit connects to a transmitter, and said transmitter sends a radio signal to a remote receiver input to said output device, and said output device is mountable remote from said existing urinal.

12. The apparatus of claim 11 wherein said output device comprises a remote indicator provided with signals from apparatus located in two said existing urinals.

13. The apparatus of claim 11 wherein said output device comprises a recorder.

14. A reusable urinalysis device comprising:

(a) a water washed, urine responsive temperature sensor responsive to temperature change to form an output signal indicative of the sensor temperature;

(b) a second urine sensor measuring a selected urine characteristic;

(c) a circuit provided with signals from both of said sensors wherein said circuit (1) is activated by a first output signal indicative of said temperature sensor response to the temperature of urine, (2) is operative responsive to urine, (3) forms a urine measurement signal while activated, and (4) is deactivated by a second output signal indicative of said temperature sensor response to wash water temperature; and (d) an output device forming a patient indicator to convey the urine measurement signal to a patient.

15. The apparatus of claim 14 including a member removably attaching said sensors to a vertical wall of an existing, wall mounted urinal as a target for a urine stream.

16. The apparatus of claim 15 wherein said member is resilient and encloses said circuit, a power supply, and a transmitter sending the urine based signal to said output device.

17. The apparatus of claim 16 wherein said circuit uses reduced power when in said off state, and more power when in said active state, thereby reducing power consumption.

18. The apparatus of claim 16 wherein said sensor makes surface contact with urine.

19. The apparatus of claim 16 wherein said apparatus positions three sensors so that said three sensors form output signals indicative of three different urine characteristics sent by said circuit to an output device responsive to three characteristics and forms a urine measurement.

20. The apparatus of claim 16 wherein said circuit connects to a transmitter, and said transmitter sends a radio signal to a remote receiver input to said output device, and said output device is mountable remote from said existing urinal.

21. The apparatus of claim 16 wherein said output device comprises a remote indicator provided with signals from apparatus located in two said existing urinals.

22. A urine test method comprising:

(a) measuring a temperature change in an existing urinal indicative of an elevated temperature associated with a stream of urine above a wash water temperature wherein said existing urinal comprises (1) a flush valve, and (2) a vertical wall across which flows wash water when said flush valve is activated;

(b) responsive to said measured temperature change, activating a sensor and contacting the urine with said sensor, wherein said sensor is responsive to a urine characteristic so that a urine measurement is made;

(c) measuring a second temperature change indicative of said wash water temperature;

(d) responsive to said second measure of temperature change, deactivating said sensor;

(e) transmitting said urine measurement in signal form; and (f) receiving the urine measurement in signal form.

23. A urinalysis device comprising:

(a) a member having:

(1) a back face for attachment to a existing urinal wherein said existing urinal comprises a flush valve, and a vertical wall across which flows flush water when said flush valve is activated, and (2) a front face exposed to a urine stream;

(b) a temperature sensor at the front face responsive to a temperature of a urine stream and to a temperature of said flush water;

(c) urine measuring sensor responsive a urine characteristic, and activated by a signal from said temperature sensor;

(d) a circuit provided with a urine sensor signal from said urine measuring sensor, and (1) activated by a signal from said temperature sensor indicative of said temperature of said urine stream, and (2) deactivated by a signal from said temperature sensor indicative of said temperature of said flush water; and (e) an output device provided with a signal from said circuit to provide a urine dependent output indication.

* * * * *

UNITED STATES PATENT AND TRADEMARK OFFICE
CERTIFICATE OF CORRECTION

PATENT NO. : 5,882,931
DATED : March 16, 1999
INVENTOR(S) : Peterson

It is certified that error appears in the above-identified patent and that said Letters Patent is hereby corrected as shown below:

On the title page, item [76], "Roger Petersen, Houston, Tex." should read -- Roger Peterson, Sweeny, Tex. --

Signed and Sealed this

Second Day of November, 1999

Attest:

Q. TODD DICKINSON

Attesting Officer

Acting Commissioner of Patents and Trademarks